United States Patent [19]

Tepi

[11] Patent Number: 4,792,339
[45] Date of Patent: Dec. 20, 1988

[54] SELF-LOCKING STEMMED COMPONENT FOR A JOINT ENDO-PROSTHESIS

[75] Inventor: Slobodan Tepi, Davos, Switzerland

[73] Assignee: Laboratorium fur Experiementelle Chirurgie, Forschungsinstitut, Davos, Switzerland

[21] Appl. No.: 5,444

[22] PCT Filed: May 23, 1985

[86] PCT No.: PCT/EP85/00251
§ 371 Date: Jan. 8, 1987
§ 102(e) Date: Jan. 8, 1987

[87] PCT Pub. No.: WO86/06954
PCT Pub. Date: Dec. 4, 1986

[51] Int. Cl.⁴ ............ A61F 2/36; A61F 2/28; A61F 2/30
[52] U.S. Cl. ............ 623/23; 623/16; 623/18; 128/303 R; 128/92 VT
[58] Field of Search ............ 623/16, 18-23

[56] References Cited

U.S. PATENT DOCUMENTS

| | | | |
|---|---|---|---|
| 4,292,695 | 10/1981 | Koeneman | 623/23 |
| 4,306,550 | 12/1981 | Forte | 128/305 X |
| 4,314,381 | 2/1982 | Koeneman | 623/22 |

FOREIGN PATENT DOCUMENTS

| | | | |
|---|---|---|---|
| 0025814 | 4/1981 | European Pat. Off. | 623/23 |
| 0085147 | 8/1983 | European Pat. Off. | 623/23 |
| 2305441 | 2/1974 | Fed. Rep. of Germany | 623/23 |
| 2726297 | 12/1978 | Fed. Rep. of Germany | 623/23 |
| 3028393 | 2/1982 | Fed. Rep. of Germany | 623/23 |
| 3441734 | 5/1985 | Fed. Rep. of Germany | 623/23 |
| 1158993 | 6/1958 | France | 128/92 YZ |
| 2502939 | 10/1982 | France | 623/23 |
| 2078523 | 1/1982 | United Kingdom | 623/22 |

Primary Examiner—Ronald L. Frinks
Attorney, Agent, or Firm—Davis Hoxie Faithfull & Hapgood

[57] ABSTRACT

A self-locking stemmed component (1) for a joint endo-prosthesis consists of two lobes (4,5) of which one (4) is designed for transfer of compression loads and the other (5) for transfer of tension loads. Both lobes (4,5) are interconnected by a number of connecting structures (6), preferably in the form of struts, which are responsive to a bending moment to produce an increase of the stem thickness upon loading of the stemmed component (1), thereby pressing the lobes (4,5) against the inner cortex of the medullary canal (23) of a tubular bone (10).

11 Claims, 10 Drawing Sheets

SELF-LOCKING STEMMED COMPONENT FOR A JOINT ENDO-PROSTHESIS

This application corresponds to. application PCT/EP85/00251 filed May 23, 1985 under the provisions of the Patent Cooperation Treaty and the benefit of the priority of said application is claimed.

This invention relates to a self-locking stemmed component for a joint endo-prosthesis, in particular for the femoral component of a hip joint prosthesis.

BACKGROUND OF THE INVENTION

Twenty-plus years of lively development in hip joint prosthesis design have not produced a fully satisfactory solution to the problem of stem loosening; it still is a major long-term complication. Current trends towards bone integration are addressing only some, perhaps minor problems of prosthesis-bone interaction.

A femoral component for an artificial hip joint is known from the German Offenlegungsschrift no. 31 13 898 in which the stem is formed by several anchoring rods which together with a collar are made from one solid casting. The rods are pressed against the inside of the bone by plugs, thereby producing a locking effect. A fixation system of this kind is not only difficult and time-consuming to insert but produces still an uncontrolled, uneven load transfer from the stemmed component of the joint endo-prosthesis to the bone with high load concentrations at the end of the stem.

SUMMARY OF THE INVENTION

The invention as claimed is intended to provide a remedy. It solves the problem of how to design a true self-locking stemmed component that can be easily inserted and removed if necessary and whose load transfer from the stem to the inner cortex of the medullary canal of a tubular bone is evenly distributed in a controlled manner. It accordance with tee invention there is provided a self-locking stemmed component for a joint endo-prosthesis whose stem thickness tends to increase when said stemmed component is loaded by physiological loads. A self-locking stemmed component in accordance with the invention is distinguished from the known constructions by its optimal adaptability to the medullary canal of the tubular bone, the ability of the stem to transmit indipendently the specific compressional, respectively tensional forces prevailing at the respective interfaces between stem and cortex in a controlled manner and as gradually and evenly as desired and the ease of its removal. Bending stiffness of the stem, a major obstacle to controlling the load transfer, is reduced manyfold by the stem geometry according to the invention.

The self-locking stemmed component consists preferably of two lobes, one for transfer of compression loads and the other for transfer of tension loads. The two lobes are destined to be pressed against the inner walls of the medullary cavity of a tubular bone by the action of connecting structures interconnecting said two lobes in such a way that relative axial displacement between said two lobes, as produced upon bending of said self locking stemmed component, increases the distance between said two lobes. The pressure for holding the two lobes in place is therefore generated by said connecting structures which are acting as wedges when the stemmed component is loaded and said two lobes are displaced in there relative axial position.

BRIEF DESCRIPTION OF THE DRAWING

In the drawing

FIGS. 7(a) and 7(b) are respectively, a sectional view of a femur and a sectional view of a femoral component with a curvature greater than that of the natural femur;

The invention is now described in more detail for the preferred use as a femoral stem component of an artificial hip joint. Of course this embodiment can be easily adapted to stemmed components of other artificial joint prosthesis.

DETAILED DESCRIPTION

Figure 1A:
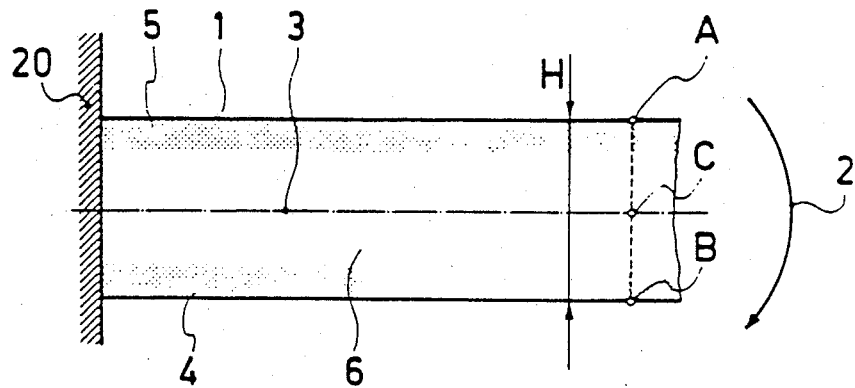
FIGS. 1(a) and 1(b) are schematic views of a stem section according to the state of the art.

FIG. 1(a) shows a generic stem design setting the requirements for a self-locking stem. Let the stem 1 be fixed to the wall 20 as a cantilever beam and be loaded by, for example, a bending moment 2. To resist the rotation under the bending moment 2, stresses within the stem 1 will develop—tension within the side 5 and compression within the side 4 of the stem 1. There will also be a neutral axis 3 between the sides 4 and 5. The sides 4 and 5 are interconnected by the connecting structure 6. Let points A, B and C lie on a normal to the neutral axis 3 as shown. H is the thickness (in the plane of load 2) of the stem 1.

Figure 1B:
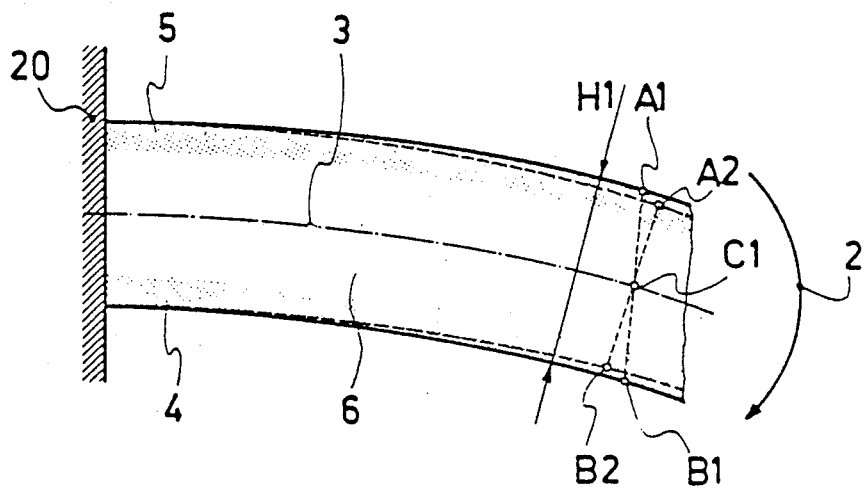

Now consider the shape of the deformed stem shown on the FIG. 1(b). The neutral axis 3 defines the so called elastic line. Thickness H1 of the stem under load is measured perpendicularly to the elastic line 3. We will now define the self-locking stem as a stem that under functional load (say the bending moment 2) INCREASES its stem thickness, i.e., H1 is greater than H. This cannot be satisfied by a simple beam. If the stem 1 was a simple beam the points A and B would move to A2 and B2 respectively. Distance (A2,B2) would remain equal to distance (A,B), i.e. the thickness H of the beam would not change under load. But, as will soon be demonstrated, the connecting region 6 may be constructed in such a way as to result in the increase of the stem thickness under functional load. Points A, B and C will move to positions A1, B1 and C1 respectively. The differences between positions A1 and B1 and those that would occur if the stem 1 was a simple beam, i.e. A2 and B2, are utilised to increase the thickness H.

Figure 2A:
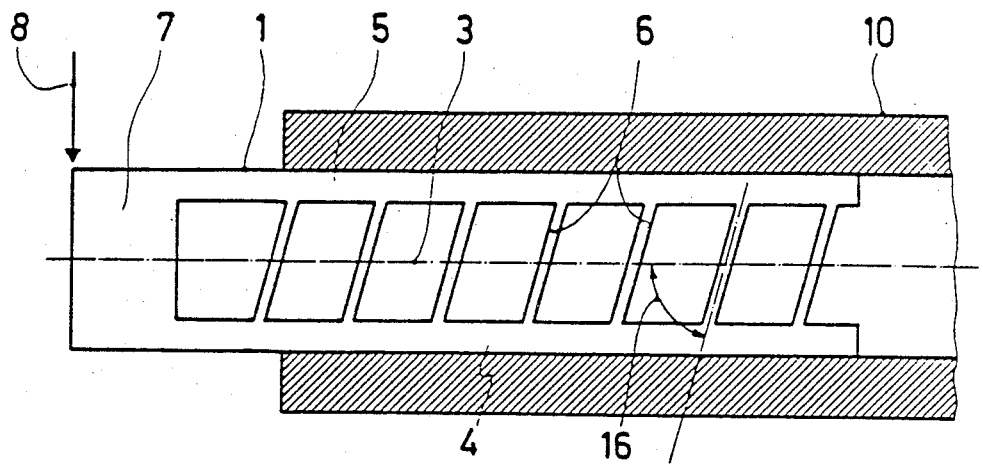
FIGS. 2(a) and 2(b) are schematic views of a stem according to the invention.

A prefered embodiment of the connecting structure 6 that will satisfy herein established criterium of self-locking is shown on FIG. 2(a). The stem 1 is shown inserted into a tubular bone 10. The load-accepting end 7 of the stem 1 is loaded by a force 8. The tension side 5 and the compression side 4 of the stem 1 are connected by a number of struts 6. These struts are inclined with respect to the neutral axis 3 of the stem 1 by an angle 16 of less than 90 degrees.

Figure 2B:
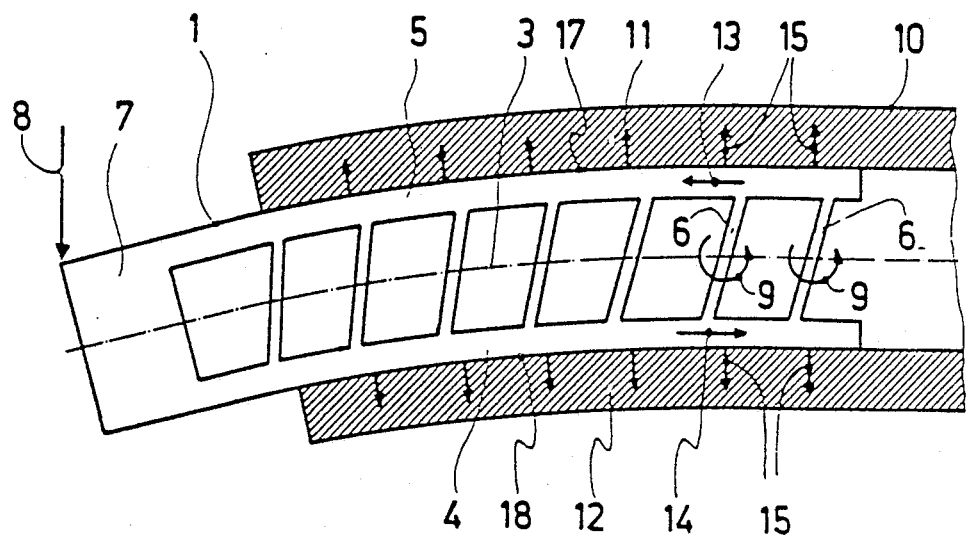

FIG. 2(b) shows deformations of the stem 1 and the bone 10 under the load 8. Tension side 5 of the stem 1 tends to pull out from the bone 10, as indicated by arrow 13, while the compression side 4 tends to sink into the bone 10, as indicated by arrow 14. This would tend to rotate the struts 6 in the direction indicated by arrows 9 producing radial compression on the bone 10, as indicated by arrows 15. These contact stresses 15 between the stem and the bone due to functional load tend to increase stability of stem anchorage. Loads are transmitted from the stem 1 to the bone 10 by the shear forces at the interfaces—tension from the side 5 of the stem 1 is transferred to the tension side 11 of the bone 10 at the interface 17; compression from the side 4 of the stem 1 to the compression side 12 of the bone 10 at the interface 18. To increase the coefficient of friction at interfaces 17 and 18 the corresponding surfaces of the stem 1 may be specially treated—for example roughened by grit blasting, or plasma sprayed.

Figure 3:
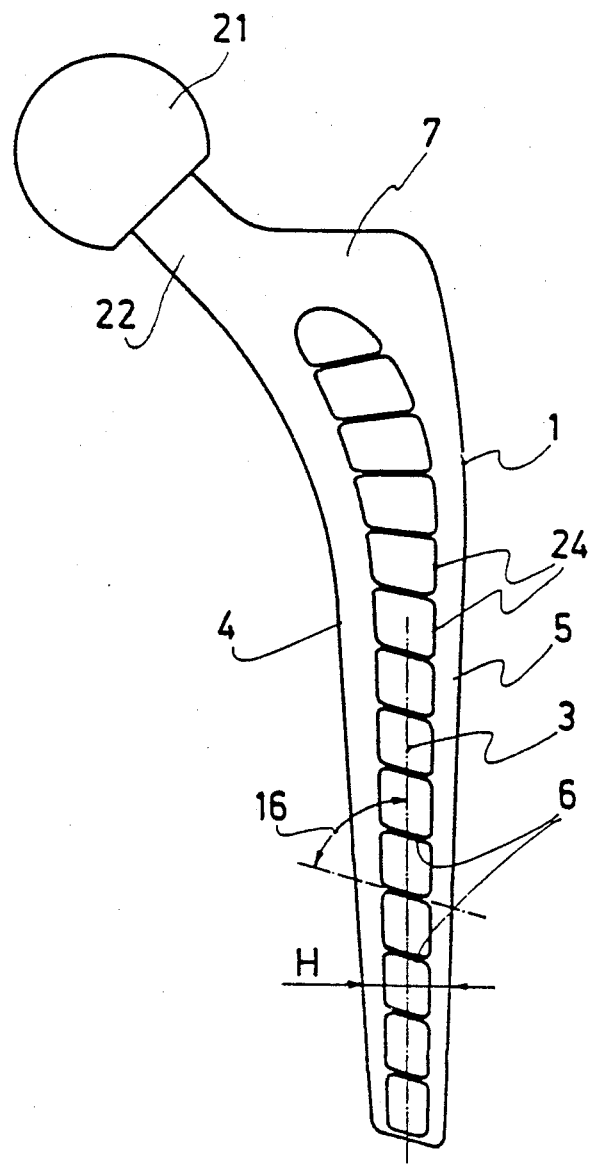
FIG. 3 is a sectional view of a femoral component for a hip joint prosthesis consisting of a self-locking stemmed component according to the invention and a joint head.

FIG. 3 shows a functional stem 1 for a femoral side component of the hip joint replacement. Prosthesis head 21 is connected to the proximal, load-accepting section 7 of the stem 1 via prosthesis neck 22. The compression side 4 is connected to the tension side 5 of the stem 1 by a number of struts 6. These struts 6 form an angle 16 with the stem neutral line 3. The angle 16 has less than 90 degrees. It may vary along the stem axis 3 in order to optimise the radial stresses 15, FIG. 2(b). The thickness H of the stem 1 also changes along the stem axis in order to fit the natural shape of the femoral bone canal 23, FIG. 5. The holes 24 between the struts 6 are cut through the full stem thickness. Some, or all of the holes 24 may be filled by an elastomer such as silicone rubber to prevent bone ingrowth—should that happen, the prosthesis removal in case of necessity would be very difficult. More proximal holes may be reached by a chisel however, so if desirable, they could be left open for bone to grow in.

Figure 4:
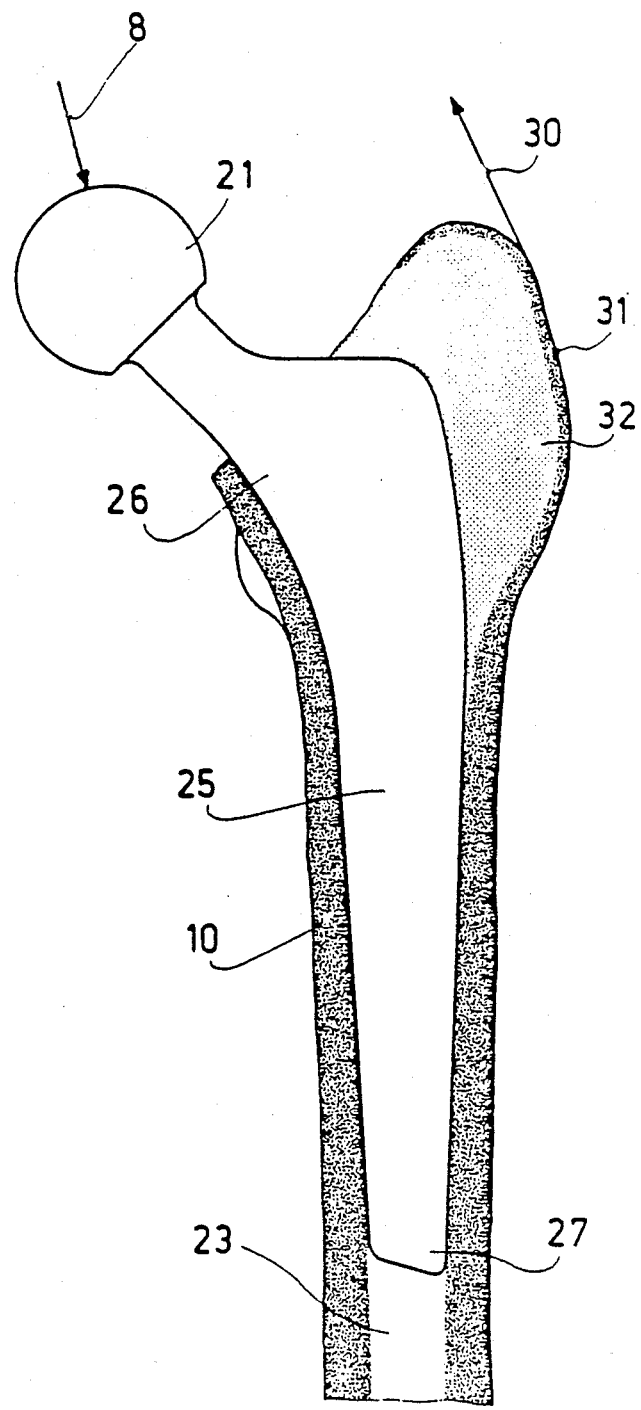
FIG. 4 is a sectional view of an implanted state-of-the-art femoral component of a hip joint prosthesis.

FIG. 4 shows a state-of-the-art femoral component of a hip prosthesis. The stem 25 is of a full cross-section. It may incorporate different surface features such as grooves, or be coated by a porous coat for bone ingrowth. The bending stiffness of these stems is very high compared to that of bone 10 and the load transfer from the prosthesis to the bone is poor—concentrated around the proximal, 26, and distal, 27, parts of the stem 25. High dynamic loads 8 applied to the head 21 of the prosthesis will result in micro-motions between the stem 25 and the bone 10 starting bone resorption within the canal 23 of the bone 10. And further, high bending stiffness of the prosthesis stem will "stress-shield" the bone—this will cause a bone loss and have a detrimental role on the long term prognosis of the joint replacement.

Figures 5, 5A:
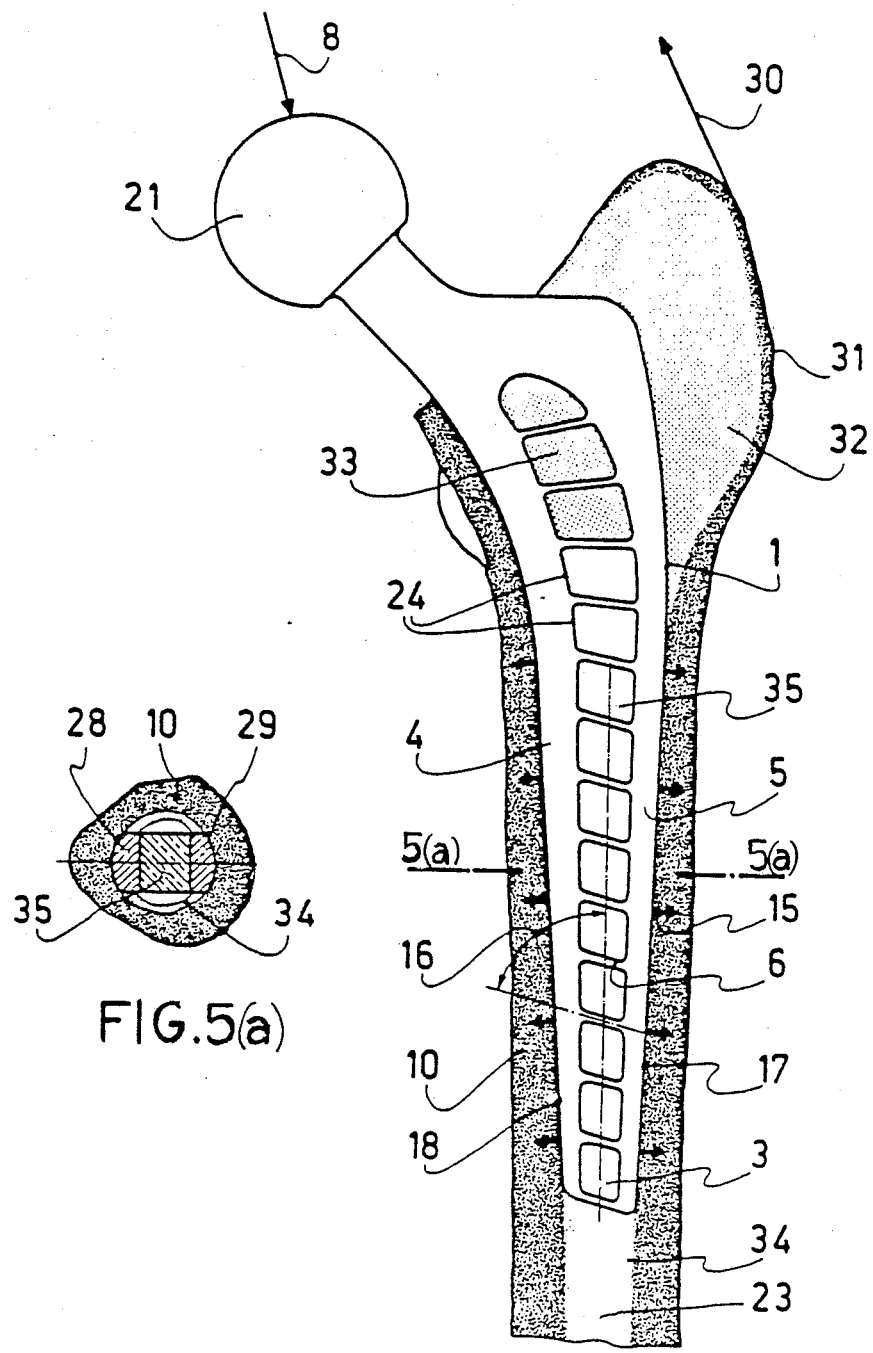
FIGS. 5 and 5(a) are respectively, a sectional view of an implanted femoral component according to the invention and a cross-sectional view of the stem taken along the line I—I.

FIG. 5 shows a femoral component stem 1 according to the invention inserted in the proximal femur 10. Note the correspondence with the situation of FIG. 2(a). Bending stiffness of the stem 1 consisting of two lobes—tensile 5 and compressive 4, connected by struts 6 is much lower than that of the full stem. Hence this stem will not cause significant stress-shielding of the bone 10. The load transfer is uniform and can be controlled by the individual cross-sections, 28 and 29, of the lobes 4 and 5, respectively. Load 8 applied to the head 21 is partitioned into compressive and tensile components and each is applied at the appropriate location of the bone. Radial stresses 15 are related to functional load and may be controlled by design (inclination 16 of the struts to the stem axis 3). The muscle force 30 is applied to the greater trochanter 31. This force is the main factor determining the magnitude and direction of the joint force 8. Most of the proximal femur is filled with cancellous bone 32. As suggested earlier, a few, more proximal holes 24 of the stem 1 may be left open to allow for cancellous bone ingrowth, 33. There is also a layer of cancellous bone 34 lining the medullary cavity 23. This should be removed where prosthesis lobes should contact bone 10, i.e. interfaces 17 and 18 should preferably be on the cortical bone. As shown on section I-I, some of the bone 34 may remain, facilitating post operative blood supply to the involved regions of the femur. More distal holes 24 are filled with an elastomer 35 to prevent bone ingrowth.

Figure 6:
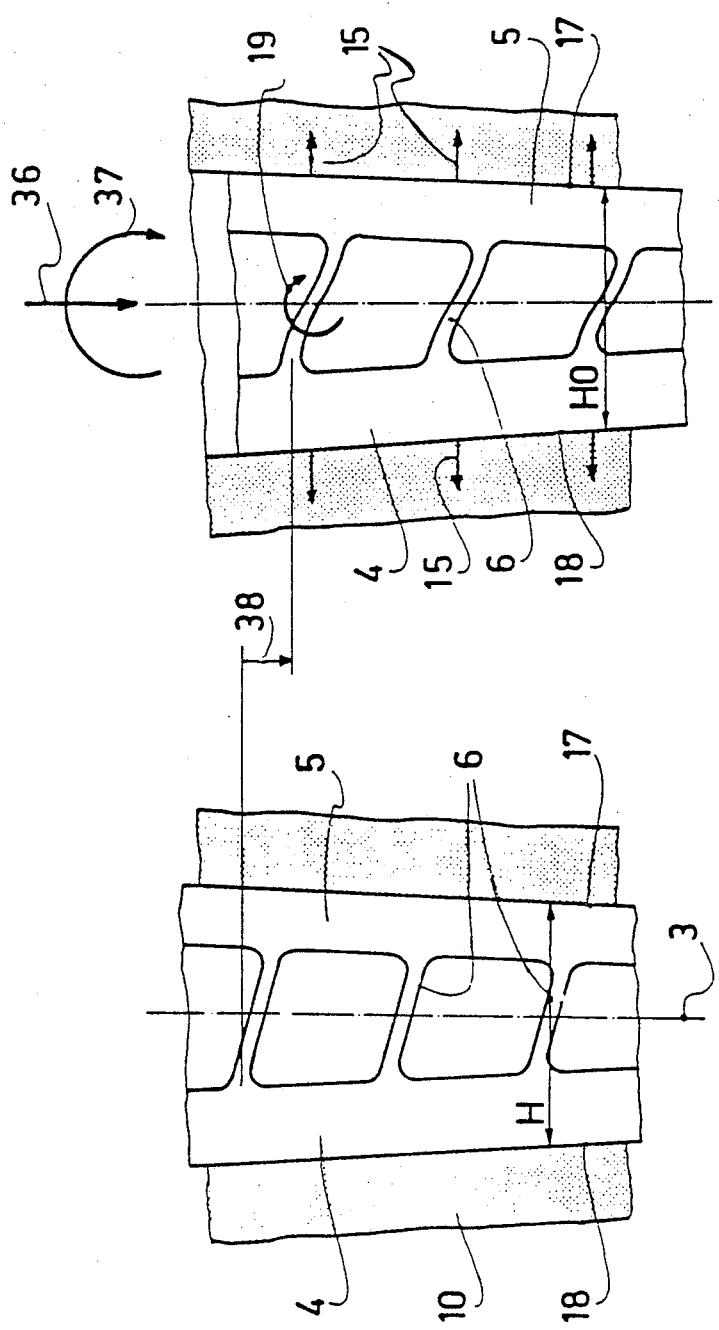
FIGS. 6(a) and 6(b) are magnified sectional views of the femoral component of FIG. 5 showing the effect of insertion.

FIG. 6 shows a magnified section of the stem at insertion. The insertion should be performed so as to result in some preload of the interfaces 17 and 18. This is possible by making use of the fact that the stem thickness will decrease when loaded by loads opposite to physiological. Hence with a bending moment 37 the struts 6 will deform as shown on FIG. 6(b). The rotation 19 will result in decreased, H0, thickness of the stem, allowing the stem to move deeper into bone 10 by amount 38 when an axial force 36 is applied. Upon release of the insertion loads 36 and 37 radial preload 15 will be set in at the interfaces 17 and 18.

Figures 7, 7A:
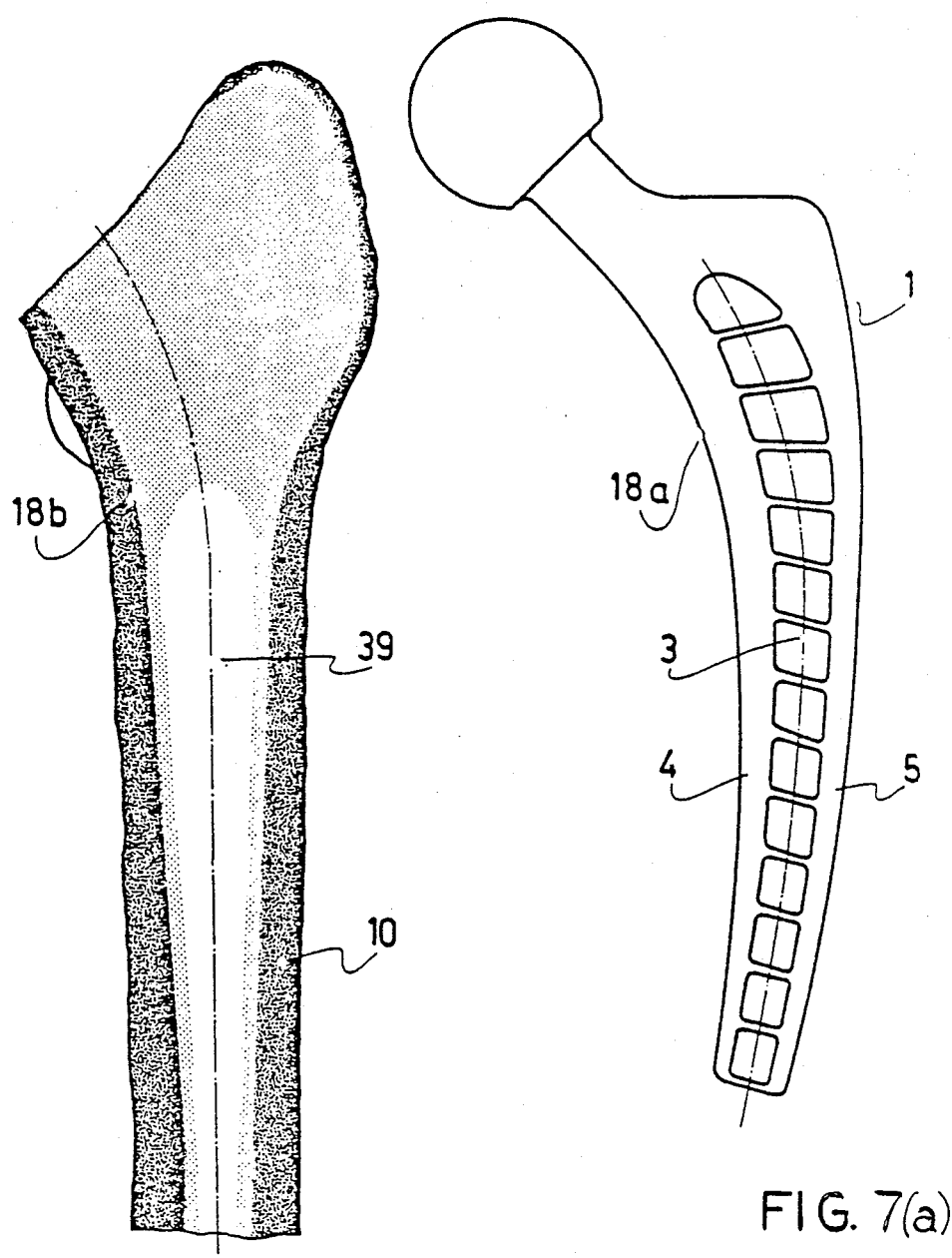

FIG. 7 shows a stem 1 according to the invention which is slightly more curved than the corresponding section of the femur, i.e. the radius of curvature of the stem's neutral line 3 is smaller than that of femur's 39. When the stem is forced into the medullary canal of a tubular bone it will bend in direction opposite to that under physiological load. Insertion will produce preloads as discussed earlier. Note also that the compression lobe 4 will be preloaded by tension and that the tension lobe 5 will be preloaded by compression. This may be of advantage in terms of stem strength. However, the preloads on bone will be of the same sign as the physiological loads, so designing for preload must be excercised with care.

Figure 8:
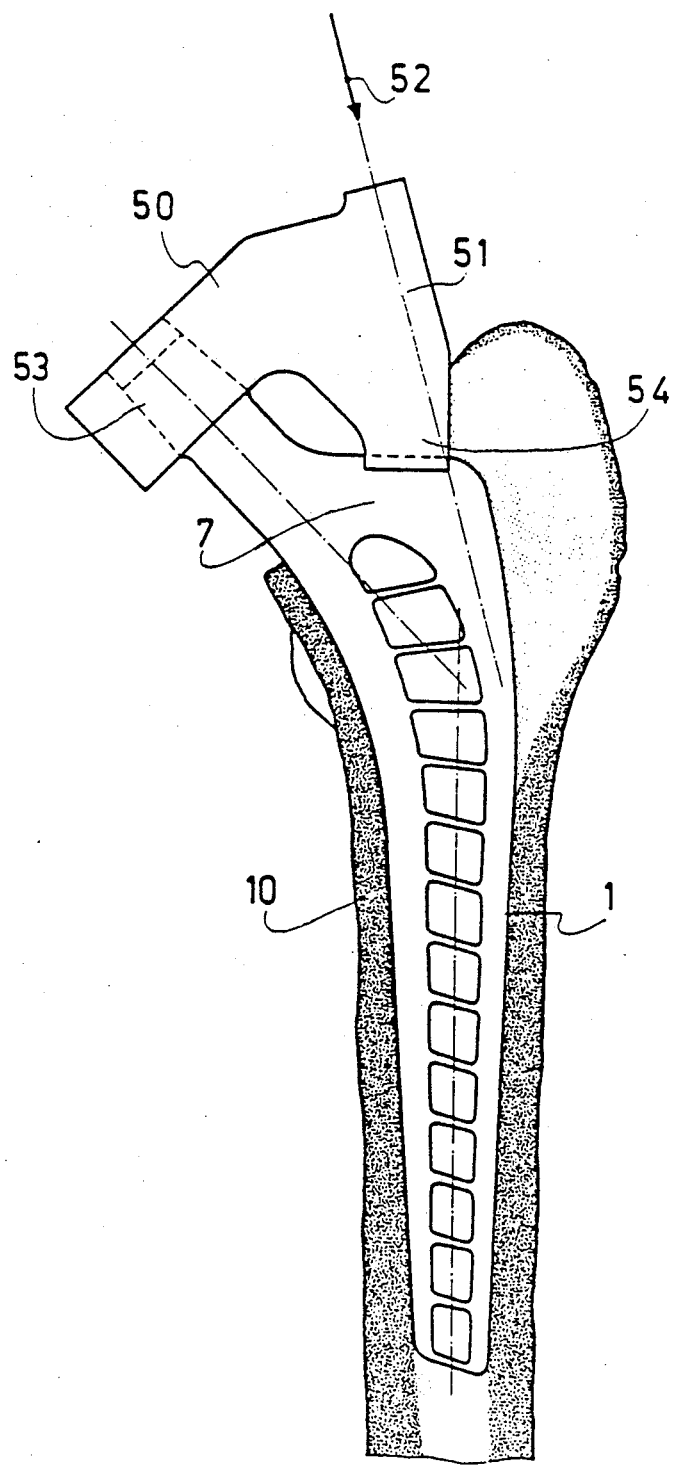
FIG. 8 is a sectional view of the inserted stemmed component according to the invention with a hammering instrument.

It is sufficient to mismatch the curvatures over only a part of the stem length. In particular, if the curvature of the proximal part of the medial side interface 18a is greater than that of the corresponding bone section 18b, the prosthesis may be inserted as described by FIG. 6 and obtain a good fit at all interfaces following insertion. Hammering the prosthesis into prepared cavity by hammer blows applied somewhat laterally as shown on FIG. 8 will produce the effects described by FIG. 6. An insertion tool 50 may be used to extend and define lateral position, 51, of the hammering force 52. The tool 50 is attached to the conus 53 of the prosthesis which normally receives the prosthesis head 21. The hammering force is transmitted to the prosthesis mainly through the extension 54 of the tool 50, resting against the proximal section 7 of the prosthesis stem.

Figure 9:
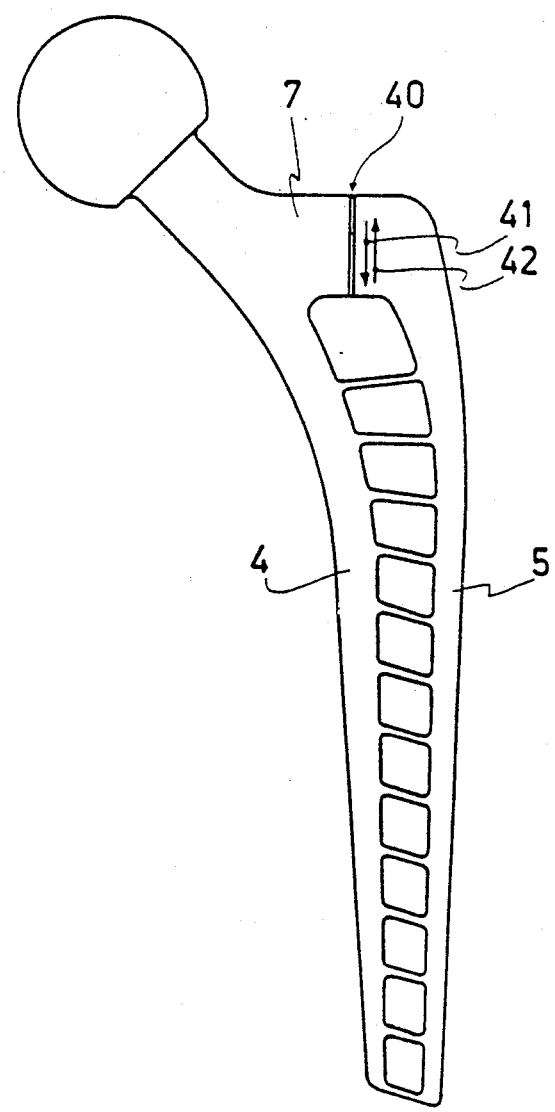
FIG. 9 is a sectional view of the stemmed component according to the invention and explaining the effect of relative axial movement between the medial and lateral lobes.

FIG. 9 shows another design feature facilitating insertion and fixation. A slot 40 is made across the section 7 of the stem. It allows relative axial sliding of the lateral lobe 5 with respect to medial lobe 4. At insertion, a displacement in direction of arrow 41 results in the reduced thickness, H of the stem 1. Fixation is accomplished by the movement in the direction of arrow 42.

Figure 10:
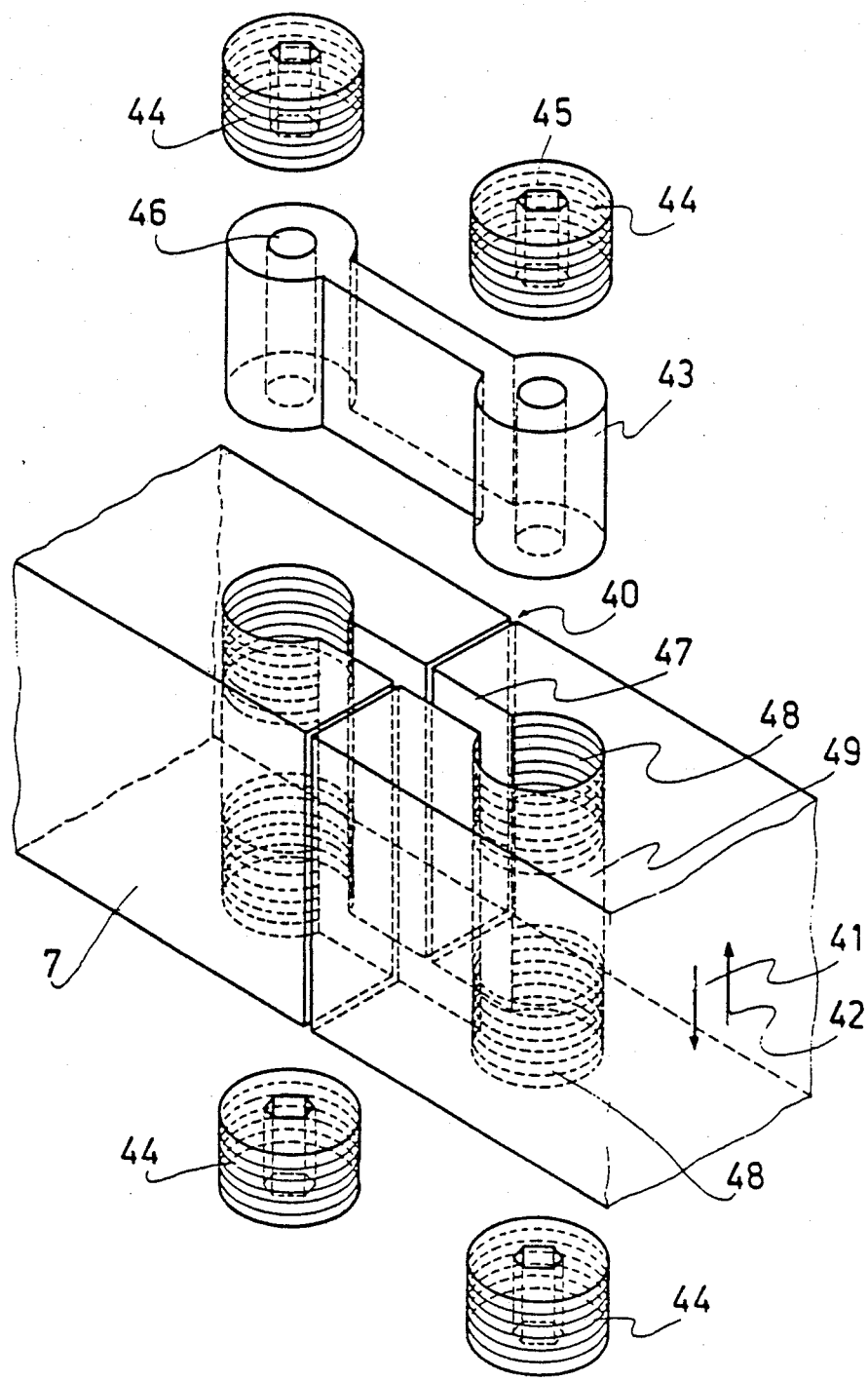
FIG. 10 is a perspective view of the means to control relative axial movements between the medial and lateral lobe of the stem.

FIG. 10 shows one possible design for the means to control movements 41 and 42. A bridge 43 is inserted into the receiving hole 47 in the section 7 of the proximal stem. This arrangement allows for parallel movement at the slot 40 while preventing the slot to open. Vertical position of the bridge 43 within the receiving hole 47 is controlled by four set-screws 44 which can be screwed into threaded portions 48 of the cylindrical sections 49 of the receiving hole 47. Cylindrical sections of the bridge 43 have clearance holes 46 so that a key can be inserted through key holes 45 of all fur screws from the top. Actually, to effect movements 41 and 42 the key is inserted through both top and bottom set screws on one side, and they are turned together moving the bridge 43 up or down in the hole 47. When desired position is achieved the top screw is tightened agains the bridge 43, fixing its position.

I claim:

1. A self-locking stem for a joint prosthesis for insertion into the medullary canal of a tubular bone, said stem having proximal and distal ends, a neutral axis, and medial and lateral lobes extending from said proximal end to said distal end and adapted to be pressed against the inner cortex of the medullary canal; and connecting means connecting said medial and lateral lobes, said connecting means being responsive to a bending moment on said stem to increase the distance between said lobes in a direction transverse to the neutral axis.

2. The self-locking stem claimed in claim 1 wherein said connecting means comprises a plurality of struts separated by apertures, at least some of said apertures being filled with elastomeric material to prevent bone ingrowth.

3. The self-locking stem claimed in claim 1 wherein the cross-section of the lobes diminishes from the proximal to the distal end.

4. The self-locking stem claimed in claim 1 wherein the exterior bone contacting surfaces of the stem are treated to increase shear strength of the bone stem interface.

5. The stem claimed in claim 4 wherein the surfaces have been grit blasted, or plasma spayed.

6. The stem claimed in claim 4 wherein the surfaces have a porous layer.

7. The stem claimed in claim 1 wherein the connecting means comprises a plurality of struts forming an angle of less than 90° with the neutral axis to optimize radial stresses.

8. The stem claimed in claim 7 wherein the struts form an angle of less than 75° with the neutral axis.

9. The stem claimed in claim 7 wherein the angle varies along the neutral axis.

10. The self-locking stem claimed in claim 1 in which the increase in the distance between said lobes under a bending movement is greater at the distal end than at the proximal end.

11. A femoral component of a hip joint prosthesis comprising the stem claimed in claim 1.

* * * * *